(12) United States Patent
Miller et al.

(10) Patent No.: US 7,402,557 B2
(45) Date of Patent: Jul. 22, 2008

(54) COMBINED TREATMENT WITH KERATINOCYTE GROWTH FACTOR AND EPIDERMAL GROWTH FACTOR INHIBITOR

(76) Inventors: Penelope Elizabeth Miller, 56 Hancock Dr., Mystic, CT (US) 06355; James Dale Moyer, 5 Jefferson Dr., East Lyme, CT (US) 06333

( * ) Notice: Subject to any disclaimer, the term of this patent is extended or adjusted under 35 U.S.C. 154(b) by 520 days.

(21) Appl. No.: 10/458,072

(22) Filed: Jun. 10, 2003

(65) Prior Publication Data

US 2004/0071697 A1 Apr. 15, 2004

Related U.S. Application Data

(63) Continuation of application No. 09/808,751, filed on Mar. 15, 2001, now abandoned.

(60) Provisional application No. 60/190,697, filed on Mar. 20, 2000.

(51) Int. Cl.
*A61K 38/18* (2006.01)
*A61K 31/675* (2006.01)
*C07D 237/00* (2006.01)

(52) U.S. Cl. .............................. 514/2; 514/12; 514/85; 544/224; 530/399

(58) Field of Classification Search .................. None
See application file for complete search history.

(56) References Cited

U.S. PATENT DOCUMENTS

| 5,747,498 A | 5/1998 | Schnur et al. |
| 5,760,041 A | 6/1998 | Wissner et al. |

FOREIGN PATENT DOCUMENTS

| WO | 94/23032 | 10/1994 |
| WO | 9625422 | 8/1996 |
| WO | 96/34614 | 11/1996 |

OTHER PUBLICATIONS

Rodeck et al. J. Cell Sci. 110: 113-121, 1997.*
Pollack et al. J. Pharmacol. Experim. Therap. 291(2): 739-748, 1999.*
Adjei, Alex. Drugs of the Future. 26(11): 1087-1092, 2001.*
Kelloff et al. Cancer Epidemiology, Biomarkers and Prevention. 5: 657-666, 1996.*
Modjtahedi et al. International Journal of Oncology 13: 335-342, 1998.*
Siu et al. American Society of Clinical Oncology, Abstract # 1498, 1999 ASCO Annual Meeting.*
Abstract Woodburn, J.R. et al. "ZD1839 An Epidermal Growth Factor Tyrosine Kinase Inhibitor Selected for Clinical Development" Asbtract only XP-001009911 dated 1997.
Driscoll, D. et al. "Effect Of Epidermal Growth Factor Receptor Tyrosine Kinase Inhibitor PD183805 On Vascular Endothelial Growth Factor Secretion From Several Tumor Models" Abstract only XP-001014746 dated 1999.
Liu et al. Am. J. Pathol. 153(1): 263-269, 1998.
Ishiwata et al. Am. J. Pathol. 153(1): 213-222, 1998.
Watanabe et al. Pathol. Internat. 50(5): 363-372, 2000.
Yang et al. "Eradication of Established-Tumors by a Fully Human Monoclonal Antibody to the Epidermal Growth Factor Receptor without Concomitant Chemotherapy" *Cancer Research* (1999) vol. 59, pp. 1236-1243.
Jones et al. "New EGF-R Selective Tyrosine Kinase Inhibitor Reveals Variable Growth Responses in Prostate Carcinoma Cell Lines PC-3 and DU-145" *Int. J. Cancer* (1997) vol. 71, pp. 1010-1018.
Groene, L., et al., "Structure-Function Relationships for the EGF/TGF-α Family of Mitogens" *Growth Factors* 11 (1994), pp. 235-257.
Wikner, N., et al. "Transforming Growth Factory-β Stimulates the Expression of Fibronectin by Human Keratinocytes" *J. Invest. Dermatology* 91 (1988), pp. 207-212.
Yoneda, A., et al., "Engineering of an FGF-proteoglycan Fusion Protein with Heparin-independent, Mitogenic Activity" *Nature Biotech.* 18 (2000) pp. 641-644.
Hsu, E., et al., "Enhanced Stability of Recombinant Keratinocyte Growth Factor by Mutagenesis" *Protein Engineering, Design & Selection* 19 (2006) pp. 147-153.
Ross, E. "Pharmacodynamis: Mechanisms of Drug Action and the Relationship Between Drug Concentration and Effect" in: *Goodman & Gilman's The Pharmacological Basis of Therapeutics* (New York, McGraw-Hill, 1996), pp. 29-31.

* cited by examiner

*Primary Examiner*—Christine J Saoud
(74) *Attorney, Agent, or Firm*—Ladas & Parry

(57) ABSTRACT

The present invention relates to compositions and methods for treating the epithelial toxicity caused by administering to a human cancer patient an epidermal growth factor receptor (EGFR) inhibitor. The pharmaceutical composition preferably comprises an EGFR inhibitor and a keratinocyte growth factor (KGF) in a pharmaceutically-acceptable carrier. The method of treatment comprises co-administering to the patient a therapeutically effective amount of KGF with the EGFR inhibitor.

16 Claims, No Drawings

COMBINED TREATMENT WITH KERATINOCYTE GROWTH FACTOR AND EPIDERMAL GROWTH FACTOR INHIBITOR

The present application is a continuation of application Ser. No. 09/808,751 filed on Mar. 15, 2001, now abandoned, which in turn claims priority from provisional application 60/190,697 filed on Mar. 20, 2000. The subject matter of each of these prior applications is incorporated herein by reference.

FIELD OF INVENTION

The present invention relates to compositions and methods for treating the epithelial toxicity resulting from the treatment of cancer patients with EGFR inhibitors. More particularly, the present invention relates to pharmaceutical compositions comprising an epidermal growth factor receptor (EGFR) inhibitor in combination with a keratinocyte growth factor (KGF), and to methods for treating the epithelial toxicity of EGFR inhibitors administered to cancer patients, comprising co-administering KGF to said patients.

BACKGROUND OF THE INVENTION

Over-expression of the epidermal growth factor receptor (EGFR), or its ligand TGFα, is frequently associated with breast, lung and head and neck cancer, and is believed to contribute to the malignant growth of these tumors. The development of compounds that inhibit the kinase activity of the EGFR, as well as antibodies that block EGFR activation, for use as anti-tumor agents is an area of intense research effort.

Epidermal growth factor (EGF), acting through its receptor EGFR, is a mitogen and survival factor for normal human keratinocytes as well as other epithelial cells (Rheinwald, J. G. and Green, H., 1977, Nature 265, 421; Rodeck, U. et al., 1997, J. Cell Science 110, 113). Thus, there is the potential that use of EGFR inhibitors in chemotherapy would interfere with the normal renewal of skin and other epithelial tissues such as the cornea and the lining of the gastrointestinal tract: Toxicity to proliferating tissues such as skin and the G1 tract is frequently a dose-limiting side effect of cytotoxic agents. Such toxicity may be manifested, among other symptoms, as a skin rash, diarrhea, corneal thinning, hair atrophy or loss, hair follicle dysplasia, degeneration, necrosis or inflammation, interfollicular epidermal hyperplasia, or a failure to heal or a delayed healing after injury.

Treatment of normal keratinocytes and EGFR over-expressing tumor cells with the EGFR inhibitor, [6,7-bis(2-methoxy-ethoxy)-quinazolin-4-yl]-(3-ethynylphenyl)amine, causes cell cycle arrest, as indicated by an accumulation of cells in the G1 phase of the cell cycle (Moyer et al., 1997, Cancer Res. 57:4838-4848). Progression of cells from the G1 phase into the S phase requires the phosphorylation of the retinoblastoma protein, pRB, which is mediated by cyclin-dependent kinases. Consistent with its ability reduce the percentage of cells in S-phase, we have observed that CP-358,774 causes depletion of hyper-phosphorylated retinoblastoma protein (ppRB) and accumulation of the cyclin-dependent kinase inhibitor, p27$^{kip1/waf1}$ (Moyer et al., supra).

The keratinocyte growth factor (KGF) family consists of KGF-1 and KGF-2, also known as FGF-7 and FGF-10, respectively, reflecting their homology with proteins in the fibroblast growth factor superfamily. Various patent publications describe KGFs and their uses, including PCT International Publication WO 94/23032, published Oct. 13, 1994; PCT International Publication WO 98/06844, published Feb. 19, 1998; PCT International Publication WO 98/16243, published Apr. 23, 1998; PCT International Publication WO 98/16642, published Apr. 23, 1998; and PCT International Publication WO 98/24813, published Jun. 11, 1998.

The KGFs are unique among FGFs in that they act exclusively on epithelial cells. Both KGFs are expressed by stromal cells and act as paracrine mediators of epithelial cell proliferation (Finch et al., 1989, Science 245:752; Igarishi et al., 1998, J. Biol. Chem. 273:13230). KGF-1 and KGF-2 are 57% homologous, and both bind to the FGFR1iiib receptor with high affinity (Igarishi et al., 1998, supra; Miceli, R., et al. 1999, J. Pharm. Exp. Ther. 290:464). Since KGFs appear to be paracrine factors in the skin (Marchese, C., et al., 1990, J. Cell Phys. 144:326; Igarashi, M., et al., 1998, supra), we investigated whether the KGF pathway can serve as an alternate means of mitogenic signaling in this tissue, thereby potentially alleviating the epithelial toxicity caused by administration of an EGFR inhibitor.

SUMMARY OF THE INVENTION

The present invention is directed to a pharmaceutical composition useful to treat the epithelial toxicity associated with administration to a patient of an epidermal growth factor receptor (EGFR) inhibitor, which pharmaceutical composition comprises an EGFR inhibitor and a keratinocyte growth factor (KGF) in a pharmaceutically acceptable carrier. In a typical treatment scenario, the EGFR inhibitor is administered as an anti-cancer agent to a patient in need thereof. In a preferred embodiment, the EGFR inhibitor is a low molecular weight inhibition or an antibody that binds specifically to the EGFR and blocks its activation.

The present invention is further directed to a method of treating the epithelial toxicity resulting from administration to a patient of an EGFR inhibitor, comprising co-administering to the patient a therapeutically effective amount of KGF with the EGFR inhibitor. In a preferred embodiment, the patient is a human that is being treated for cancer. In a further preferred embodiment, the epithelial toxicity is manifested as a skin toxicity.

The present invention is further directed to a method of preparing a pharmaceutical composition useful for treating the epithelial toxicity resulting from administration to a patient of an EGFR inhibitor, comprising combining an EGFR inhibitor with a keratinocyte growth factor (KGF). In a preferred embodiment, the method further comprises combining a pharmaceutically acceptable carrier with the EGFR inhibitor and KGF.

The present invention further provides a kit comprising a first container comprising an EGFR inhibitor, and a second container comprising a KGF. A pharmaceutically acceptable carrier may also be present in either container. The kit may further comprise a third container comprising a sterile diluent. The kit may further comprise a package insert comprising printed instructions directing the use of the combined treatment as a method for treating the epithelial toxicity resulting from administration to a patient of an EGFR inhibitor.

DETAILED DESCRIPTION OF THE INVENTION

The data presented in the Examples herein below demonstrate that co-administration of a KGF with an EGFR inhibitor is effective at protecting human epithelial keratinocytes from the cell cycle arrest normally induced by the EGFR inhibitor alone. Thus, KGF can advantageously be used to protect normal epithelial cells from the toxicity otherwise caused by administering an EGFR inhibitor alone to a patient. Accordingly, the present invention provides a pharmaceutical composition comprising an EGFR inhibitor and a KGF in a pharmaceutically acceptable carrier.

As used herein, the term "EGFR inhibitor" refers to any EGFR inhibitor that is currently known in the art or that will be identified in the future, and includes any chemical entity that, upon administration to a patient, results in inhibition of a biological activity associated with activation of the EGFRs in the patient, including any of the downstream biological effects otherwise resulting from the binding to an EGFR of its natural ligand. Such EGFR inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor or a portion thereof, thereby making the receptor inaccessible to its natural ligand so that its normal biological activity is prevented or reduced. EGFR inhibitors include but are not limited to low molecular weight inhibitors, antibodies or antibody fragments, antisense constructs and ribozymes. In a preferred embodiment, the EGFR inhibitor is a small organic molecule or an antibody that binds specifically to the human EGFR.

EGFR inhibitors that can be used according to the present invention include but are not limited to those classified in the art as quinazoline EGFR inhibitors, pyrido-pyrimidine EGFR inhibitors, pyrimido-pyrimidine EGFR inhibitors, pyrrolo-pyrimidine EGFR inhibitors, pyrazolo-pyrimidine EGFR inhibitors, phenylamino-pyrimidine EGFR inhibitors, oxindole EGFR inhibitors, indolocarbazole EGFR inhibitors, phthalazine EGFR inhibitors, isoflavone EGFR inhibitors, quinalone EGFR inhibitors, and tyrphostin EGFR inhibitors.

Non-limiting examples of low molecular weight EGFR inhibitors useful in practicing the present invention include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 1997; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510, published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of low molecular weight EGFR inhibitors include any of the EGFR inhibitors described in Traxler, P., 1998, Exp. Opin. Ther. Patents 8(12):1599-1625.

Specific preferred examples of low molecular weight EGFR inhibitors that can be used according to the present invention include [6,7-bis(2-methoxyethoxy)-4-quinazolin-4-yl]-(3-ethynylphenyl)amine (U.S. Pat. No. 5,747,498 issued May 5, 1998 and Moyer et al., 1997, supra); C1-1033 and PD183805 (Sherwood et al., 1999, Proc. Am. Assoc. Cancer Res. 40:723); and ZD1839 (Woodburn et al., 1997, Proc. Am. Assoc. Cancer Res. 38:633).

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

Additional antibody-based EGFR inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR inhibitors useful in practicing the present invention also include anti-EGFR antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are additionally described, among other places, in Harlow and Lane, 1988, Antibodies: A Laboratory Manual, Cold Spring Harbor Laboratory, and in J. W. Goding, 1986, Monoclonal Anti-bodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation. For example, antisense oligonucleotides of at least about 15 bases and complementary to unique regions of the mRNA transcript sequence encoding EGFR can be synthesized, eg., by conventional phosphodiester techniques and administered by e.g., intravenous injection or infusion.

Ribozymes can also function as EGFR inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both anti-sense oligonucleotides and ribozymes useful as EGFR inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

As used herein, "keratinocyte growth factor", or "KGF" refers to KGF-1 and KGF-2. The nucleotide and amino acid sequences of KGF-1 are described in Finch et al., 1989, Science 245:752-755. The amino acid sequence of KGF-2 is described in Igarishi et al., 1998, J. Biol. Chem. 273:13230.

Native KGF may be isolated from native human sources or produced by recombinant DNA techniques, as known in the art. Human recombinant KGF-1, as expressed from *E. Coli*, is a 19 kDa protein, and is commercially available (Sigma Chemical Co., St. Louis, Mo.). KGF analogs reportedly having increased stability over natural KGF are described in PCT International Publication WO 96/11951, which published Apr. 25, 1996, and such KGF analogs can be used as the KGF component in practicing the present invention. Alternatively, any fragment of the entire KGF polypeptide or analog thereof which fragment or analog retains complete or even partial KGF activity can be as used in practicing the present invention. Alternatively, KGF-2, as disclosed in PCT International Publication WO 98/06844 which published Feb. 19, 1998, or any analogs or peptide fragments thereof retaining complete or partial KGF-2 activity, can be used as the KGF component in practicing the present invention. Unless otherwise indicated, all alternative forms of KGF and KGF analogs useful in practicing the present invention are referred to collectively hereinafter as "KGF".

The present invention further provides a method for treating the epithelial toxicity resulting from administration to a patient of an EGFR inhibitor, comprising co-administering to the patient a therapeutically effective amount of KGF With the EGFR inhibitor.

The term "treating" as used herein, unless otherwise indicated, means reversing, alleviating, inhibiting the progress of, or preventing, either partially or completely, the epithelial toxicity, or one or more conditions or symptoms associated with the epithelial toxicity, caused by administration to a patient of a dose (single or divided) or series of doses (e.g., a course of treatment) of an EGFR inhibitor useful in treating cancer. The term "treatment" as used herein, unless otherwise indicated, refers to the act of treating as "treating" is defined immediately above.

As used herein, the term "epithelial toxicity" refers to an abnormality or dysfunction of the epithelium, and can be manifested in a patient being treated for cancer by administration of an EGFR inhibitor by one or more symptoms or conditions selected from skin rash, diarrhea, corneal thinning, hair atrophy or loss, hair follicle dysplasia, degeneration, necrosis or inflammation, interfollicular epidermal hyperplasia, or a failure to heal or a delayed healing after injury, among other symptoms.

In a preferred embodiment, the epithelial toxicity is manifested as a skin toxicity such as acneform or macro-papular rash.

As used herein, the term "patient" preferably refers to a human in need of treatment with an EGFR inhibitor for any purpose, and more preferably a human in need of such a treatment to treat cancer. However, the term "patient" can also refer to non-human animals, preferably mammals such as dogs, cats, horses, cows, pigs, sheep and non-human primates, among others, that are in need of treatment with an EGFR inhibitor.

In a preferred embodiment, the patient is a human in need of treatment for cancer. The cancer is preferably any cancer treatable, either partially or completely, by administration of an EGFR inhibitor. The cancer may be selected from, but is not limited to, the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), spinal axis tumors, brain stem glioma, pituitary adenoma, or a combination of one or more of the foregoing cancers.

In another embodiment of said method, the patient is a human being that is in need of treatment for a benign proliferative disease, including, but not limited to, psoriasis, benign prostatic hypertrophy or restenosis.

For purposes of the present invention, "co-administration of" and "co-administering" KGF with an EGFR inhibitor (both components referred to hereinafter as the "two active agents") refer to any administration of the two active agents, either separately or together, where the two active agents are administered as part of an appropriate dose regimen designed to obtain the protective benefit of the combination therapy. Thus, the two active agents can be administered either as part of the same pharmaceutical composition or in separate pharmaceutical compositions. KGF can be administered prior to, at the same time as, or subsequent to administration of the EGFR inhibitor, or in some combination thereof, as long as the patient obtains the protective effect of KGF against the epithelial toxicity that might otherwise be caused by administration of the EGFR inhibitor alone. Where the EGFR inhibitor is administered to the patient at repeated intervals, e.g., during a standard course of treatment, KGF can be administered prior to, at the same time as, or subsequent to, each administration of the EGFR inhibitor, or some combination thereof, or at different intervals in relation to the EGFR inhibitor treatment, or in a single dose prior to, at any time during, or subsequent to the course of treatment with the EGFR inhibitor, so long as the patient obtains the protective effect of KGF against the epithelial toxicity that might otherwise be caused by administration of the EGFR inhibitor alone.

The EGFR inhibitor will typically be administered to the patient in a dose regimen that provides for the most effective treatment of the cancer (from both efficacy and safety perspectives) for which the patient is being treated, as known in the art, and as disclosed, e.g., in the above-cited publications. In conducting the treatment method of the present invention, the EGFR inhibitor can be administered in any effective manner as known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of EGFR inhibitor being used (e.g., small molecule, antibody or antisense construct), and the medical judgement of the prescribing physician as based, e.g., on the results of published clinical studies.

The amount of EGFR inhibitor administered and the timing of EGFR inhibitor administration will depend on the type (species, gender, age, weight, etc.) and condition of the patient being treated, the severity of the disease or condition being treated, and on the route of administration. For example, small molecule EGFR inhibitors can be administered to a patient in doses ranging from 0.01 to 10 mg/kg of body weight per day or per week in single or divided doses, or by continuous infusion. Antibody-based EGFR inhibitors, or antisense or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, a "therapeutically effective amount of KGF" refers to that amount of KGF capable of reversing, alleviating, inhibiting the progress of, or preventing, either completely or partially, one or more symptoms or conditions in a patient resulting from epithelial toxicity caused by administration to the patient of a standard dose or series of doses (e.g., a standard course of treatment) of an EGFR inhibitor administered to the patient for the treatment of cancer or other disease, disorder or condition. The therapeutically effective amount of KGF can be administered as a single dose, as several divided doses, or can be continuously infused.

The prescribing physician can determine what constitutes a "therapeutically effective amount of KGF" based initially, e.g., on the results of published clinical trials, and the recommended dose described in any package insert as present in a kit comprising the two active agents. The dose of KGF can be adjusted up or down by the prescribing physician depending on the degree of responsiveness to KGF treatment by the particular patient. The prescribing physician will preferably monitor responses to the co-administration treatment, particularly as those responses relate to prevention or amelioration of epithelial toxicity otherwise associated with administration of the EGFR inhibitor alone. In a preferred embodiment, the prescribing physician will monitor the condition of the patient's skin, and particularly the prevention or improvement in any skin rash caused by or otherwise associated with administration of the EGFR inhibitor. In a further preferred embodiment, the prescribing physician, by opthalmalogical exam, will monitor corneal thinning in the patient caused by or otherwise associated with administration of the EGFR inhibitor. In a further preferred embodiment, the prescribing physician will monitor diarrhea in the patient caused by or otherwise associated with administration of the EGFR inhibitor.

The KGF will typically be administered to the patient in a dose regimen that provides for the most effective and safest treatment of the epithelial toxicity caused by the EGFR inhibitor, or of one or more conditions or symptoms associated with the epithelial toxicity. The KGF can be administered in a convenient manner as known in the art, such as by topical, intravenous, intraperitoneal, intramuscular, intra-articular, subcutaneous, intranasal, intraocular, vaginal, rectal or intradermal routes, as determined by the prescribing physician.

The amount of KGF administered and the timing of KGF administration will depend on the type (species, gender, age, weight, etc.) and condition of the patient being treated, the severity or potential severity of the epithelial toxicity caused by the EGFR inhibitor, the route of administration, and the judgement of the prescribing physician as based, e.g., on the results of published clinical studies. For example, KGF can be administered parenterally to a patient in doses ranging from 0.01 to 10 mg/kg of body weight per day or somewhat less frequently such as 1-4 times per week in single or divided doses. Also, for example, KGF can be administered topically to a patient once or more per day in formulations comprising from about 0.001% (w/v) to about 1.0% (w/v). In some instances, dosage and concentration levels below the lower limit of the aforesaid ranges may be more than adequate, while in other cases still larger doses or concentrations may be employed without causing any harmful side effects, provided that such larger doses are first divided into several small doses for administration throughout the day. In some circumstances, a single treatment or series of treatments with KGF will be sufficient to treat the epithelial toxicity caused by the EGFR inhibitor, while in other circumstances the treatment will continue until sufficient improvement in the condition is observed by the attending physician, as determined by one or more standard indices of epithelial toxicity such as corneal epithelial thickness as determined, e.g., by a slit-lamp test.

The present invention further provides a method of preparing a pharmaceutical composition useful for treating the epithelial toxicity resulting from administration to a patient of an EGFR inhibitor, comprising combining an EGFR inhibitor with KGF. In a preferred embodiment, the method further comprises combining a pharmaceutically acceptable carrier with the EGFR inhibitor and KGF.

The present invention further provides a use for an EGFR inhibitor combined with KGF in preparing a medicament for heating cancer in a patient while also treating the epithelial toxicity resulting from administration to a patient of the EGFR inhibitor alone. The present invention further provides a use for co-administered EGFR inhibitor and KGF in preparing an anti-cancer treatment having reduced epithelial toxicity.

The EGFR inhibitors and KGF can be administered either separately or together by the same or different routes, and in a wide variety of different dosage forms. For example, the EGFR inhibitor is preferably administered orally or parenterally, whereas KGF is preferably administered parenterally or topically.

The EGFR inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The KGF can be administered with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media and various non-toxic organic solvents, etc.

The EGFR inhibitor and KGF can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media and, various non-toxic organic solvents, etc.

All formulations comprising KGF should be selected so as to avoid denaturation and loss of biological activity of the KGF polypeptide.

Methods of preparing pharmaceutical compositions comprising an EGFR inhibitor are known in the art, and are described, e.g., in several of the above-cited publications. Methods of preparing pharmaceutical compositions comprising KGF are also known in the art, and are described, e.g., in several of the above-cited publications. In view of the teaching of the present invention, methods of preparing pharmaceutical compositions comprising both an EGFR inhibitor and KGF will be apparent from the above-cited publications and from other known references, such as *Remington's Pharmaceutical Sciences*, Mack Publishing Company, Easton, Pa., 18th edition (1990).

For oral administration of EGFR inhibitor, tablets containing one or both of the active agents are combined with any of various excipients such as microcrystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of KGF should be selected so as to avoid denaturation and loss of biological activity of the KGF polypeptide.

Additionally, it is possible to topically administer either or both of the active agents, and this may preferably be done by way of creams, lotions, jellies, gels, pastes, ointments, salves and the like, in accordance with standard pharmaceutical practice. For example, a topical formulation comprising either an EGFR inhibitor or KGF in about 0.1% (w/v) to about 5% (w/v) concentration can be prepared. In a preferred embodiment, a topical formulation of KGF can be prepared and will be particularly effective where the epithelial toxicity caused by the EGFR inhibitor is manifested as a skin toxicity.

Any topical formulation selected for KGF should be selected so as to avoid denaturation and loss of biological activity of the KGF polypeptide.

For veterinary purposes, the active agents can be administered separately or together to animals using any of the forms and by any of the routes described above. In a preferred embodiment, the EGFR inhibitor is administered in the form of a capsule, bolus, tablet, liquid drench, by injection or as an implant. As an alternative, the EGFR inhibitor can be administered with the animal feedstuff and for this purpose a concentrated feed additive or premix may be prepared for a normal animal feed. The KGF is preferably administered in the form of liquid drench, by injection or as an implant. Such formulations are prepared in a conventional manner in accordance with standard veterinary practice.

The present invention further provides a kit comprising a single container comprising both an EGFR inhibitor and KGF. The present invention further provides a kit comprising a first container comprising an EGFR inhibitor and a second container comprising KGF. In a preferred embodiment, the kit containers may further comprise a pharmaceutically acceptable carrier. The kit may further comprise a sterile diluent, which is preferably stored in a separate additional container. The kit may further comprise a package insert comprising printed instructions directing the use of the combined treatment as a method for treating the epithelial toxicity resulting from administration to a patient of an EGFR inhibitor.

The following examples are illustrative only, and are not intended to limit the scope of the present invention.

EXAMPLE 1

Measuring Protection of Keratinocytes by KGF

The protective effect of KGF on keratinocytes was measured in two types of assays, the first to determine its protective effect on cell cycle phase distribution against a small molecule EGFR inhibitor, and the second to determine its protective effect against ppRB depletion and $p27^{kip1/waf1}$ upregulation caused by the EGFR inhibitor. The effect of KGF on cell cycle phase distribution was measured by bivariate analysis of bromodeoxyuridine incorporation and propidium iodide uptake by DiFi colon carcinoma cells using flow cytometry. The protective effect of KGF against ppRB depletion and $p27^{kip1/waf1}$ upregulation was measured by immunoblotting of lysates from treated and control DiFi cells with antibodies specific for RB and $p27^{kip1/waf1}$, respectively. The methods are described in detail below.

All experiments were carried out with normal human neonatal epidermal keratinoctyes, NHEK (Clonetics, San Diego, Calif.). Cells were maintained in Keratinocyte Growth Medium, KGM-2 (Clonetics). Human recombinant KGF expressed in *E. coli* as a 19 kDa protein was purchased from Sigma Chemical Co. (St. Louis, Mo.).

Flow Cytometric Measurement of Cell Cycle Arrest

NHEK cells were seeded in 60-mm dishes in KGM-2. When the cells were semiconfluent, the medium was replaced with fresh medium containing the test agents: vehicle (0.125% DMSO); vehicle+20 ng/ml KGF; vehicle+0.3 µM CP-358, 774-01+/−20 ng/ml KGF; or vehicle+1 µM CP-358, 774-01+/−20 ng/ml KGF. The cells were incubated at 37° C. in a 5% $CO_2$, humidified atmosphere. After 24 hr, bromodeoxyuridine (BrdU) was added to the medium at a final concentration of 10 µM for 30 min. The cells were then harvested using 0.25% trypsin/1 mM EDTA and counted using a Coulter counter. Aliquots of $2\times10^6$ cells were collected by centrifugation at 220×g for 5 min, washed in 2 ml phosphate buffered saline (PBS) containing 2.5% fetal calf serum, resuspended in 0.2 ml PBS, and fixed by the addition of 5 ml 70% ethanol at −20° C. After a 30 min incubation on ice, the cells were collected by centrifugation at 500×g for 5 min and resuspended in 25 µl PBS. One ml of 0.2 mg/ml pepsin in 2 N HCl was added and the cells were incubated for 30 min at rm temp. Cells were collected by centrifugation at 1500×g for 5 min and washed with 1 ml 0.1 M sodium borate, pH 8.5. Cells were pelleted at 1500×g for 5 min, resuspended in 1 ml of fluorescein isothiocyanate (FITC)-conjugated anti-BrdU (Becton Dickinson, San Jose, Calif.) diluted fifty-fold in PBS containing 0.5% Tween 20 and 1% bovine serum albumin, and incubated at ambient temperature in the dark for 30 min. After a final wash with PBS with 0.5% Tween 20 and 1% BSA, the cells were resuspended in PBS containing 10 µg/ml propidium iodide and 10 µg/ml RNase, filtered through a 35 pm mesh and analyzed on a FACSCalibur flow cytometer (Becton Dickinson) equipped with an argon laser with an emission wavelength of 488 nm. FITC fluorescence data was acquired at 515-545 nm, and propidium iodide fluorescence data was acquired at 564-606 µm. A minimum of 20,000 cells was analyzed per sample. Data was analyzed using CellQuest software (Becton-Dickinson) and the percent of cells in each phase (G1, S, G2) of the cell cycle was calculated.

Measurement of PPRB and $P27^{KIP1/WAF1}$ Protein Levels

NHEK cells were seeded in 6-well plates and grown until semi-confluent in KGM-2. Fresh medium containing vehicle or CP-358, 774-01+/−20 ng/ml KGF was added, and the cells were incubated for 24 hr in a 5% $CO_2$, humidified atmosphere. Cells were washed with 50 mM Tris-HCl pH 7.4, 140 mM sodium chloride, 3.3 mM potassium chloride and 500 µM sodium orthovanadate, and lysed by boiling for 10 min in SDS sample buffer (50 mM Tris-HCl, pH 6.8, 100 mM DTT, 2% SDS, 0.1% bromphenol blue, 10% glycerol). Total protein concentration of the lysates was determined using the BCA protein assay (Pierce Chemicals, Rockford, Ill.). Ten µg of protein was resolved on a 7.5% (RB) or 4-20% (p27) polyacrylamide gel (Owl Separation Systems, Portsmouth, N.H.), and transferred to an Immobilon-P membrane (Millipore, Bedford, Mass.) for 2 hr at 250 mA. Membranes were blocked overnight in 4% nonfat dry milk in TBST (50 mM Tris-HCl, pH 7.4, 150 mM NaCl, and 0.1% Tween 20) and probed with 1 µg/ml monoclonal antibody G3-245 (Pharmingen, San Diego, Calif.) for RB detection or with 0.1 µg/ml anti-p27kip1 Clone 57 monoclonal antibody (Transduction Labs, Lexington, Ky.) followed by horseradish peroxidase-conjugated goat anti-mouse IgG (Pharmingen) diluted 1:1000. The identity of the lower band in RB blots as hypo-phosphorylated RB (pRB) was confirmed by use of an antibody, Clone G99-549 (Pharmingen), specific for this form.

Results

Cell Cycle Phase Distribution

Treatment of keratinocytes for 24 hours with N-(3-ethynylphenylamino)-6,7-bis(2-methoxyethoxy-4-quinazolineamine hydrochloride salt (Compound A) caused a concentration dependent accumulation of cells in the G1 phase of the cell cycle and a corresponding decrease in the S-phase fraction (Table 1). Co-treatment with KGF reversed this effect, while treatment with KGF alone had no significant effect on cell cycle phase distribution.

TABLE 1

| Treatment | % G1 | % S | % G2 |
|---|---|---|---|
| Vehicle | 52 | 34 | 12 |
| 20 ng/ml KGF | 52 | 34 | 13 |
| 0.3 μM Compound A | 75 | 13 | 11 |
| 0.3 μM Compound A + 20 ng/ml KGF | 53 | 34 | 12 |
| 1 μM Compound A | 85 | 6.0 | 10 |
| 1 μM Compound A + 20 ng/ml KGF | 50 | 35 | 13 | ppRB and p27$^{kip1/waf1}$ Levels

Hyperphosphorylated (ppRB) and hypophosphorylated (pRB) retinoblastoma protein can be resolved because of their different rates of migration on polyacrylamide electrophoresis gels. Both forms of the protein have a MW of ~105 kDa, but ppRB migrates slower than pRB, resulting in the appearance of an upper (ppRB) and/or a lower (pRB) band on blots that have been probed with the monoclonal antibody, G3-245, which recognizes both forms of the protein.

In untreated proliferating keratinocytes, all apparent RB immuno-reactivity was in the hyperphosphorylated RB (upper band). After treatment with 0.3 μM Compound A, the ppRB signal was dramatically reduced and a lower band corresponding to pRB appeared. However, cells treated simultaneously with both 0.3 μM Compound A and 20 ng/ml KGF resembled control cells and exhibited only the upper band. Thus, despite the presence of the EGFR inhibitor, these cells contained predominantly hyperphosphorylated RB (i.e., the form of RB that is permissive for cell cycle progression). This is consistent with the BrdU labeling assay described above, in which cells treated simultaneously with Compound A and KGF had an S-phase fraction similar to that of controls. In keratinocytes treated with 1 μM Compound A, the ppRB band was completely abolished and, as at the lower concentration of Compound A, co-treatment with KGF completely restored ppRB to control levels.

pRB is phosphorylated by cyclin-dependent kinases (cdk's), which are positively regulated by cyclins and negatively regulated by the cdk inhibitors p21$^{cip1}$ and p27$^{kip1/waf1}$. Lysates of keratinocytes treated with 0.3 μM Compound A exhibited a 3.9-fold induction of p27$^{kip1/waf1}$ protein levels, consistent with the effect of the compound on pRB phosphorylation. Treatment with 1 μM Compound A resulted in a 5.2-fold induction of p27$^{kip1/waf1}$. Co-treatment with KGF partially restored p27$^{kip1/waf1}$ to control levels.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

The invention claimed is:

1. A method of treating the epithelial toxicity resulting from administration to a patient of the EGFR inhibitor N-(3-ethynylphenylamino)-6,7-bis(2-methoxyethoxy)-4-quinazoline amine or a pharmaceutically acceptable salt thereof, comprising co-administering to the patient a therapeutically effective amount of KGF with the EGFR inhibitor.

2. The method of claim 1, wherein the patient is a human that is being treated for cancer.

3. The method of claim 1, wherein the epithelial toxicity is a skin toxicity.

4. The method of claim 3, wherein the skin toxicity is manifested as a rash.

5. The method of claim 1, wherein the epithelial toxicity is manifested as corneal thinning.

6. The method of claim 1, wherein the epithelial toxicity is manifested as diarrhea.

7. The method of claim 1, wherein the EGFR inhibitor and KGF are co-administered to the patient in the same formulation.

8. The method of claim 1, wherein the EGFR inhibitor and KGF are co-administered to the patient in different formulations.

9. The method of claim 1, wherein the EGFR inhibitor and KGF are co-administered to the patient by the same route.

10. The method of claim 1, wherein the EGFR inhibitor and KGF are co-administered to the patient by different routes.

11. The method of claim 1, wherein the EGFR inhibitor is administered to the patient by parenteral or oral administration.

12. The method of claim 1, wherein KGF is administered to the patient by parenteral or topical administration.

13. The method of claim 1, wherein the KGF is human KGF-1, or an analog thereof having at least partial human KGF-1 activity.

14. The method of claim 1, wherein the KGF is human KGF-2, or an analog thereof having at least partial human KGF-2 activity.

15. A method of preparing a pharmaceutical composition useful for treating the epithelial toxicity resulting from administration to a patient of an EGFR inhibitor, comprising combining a KGF with the EGFR inhibitor.

16. The method of claim 15, further comprising combining a pharmaceutically acceptable carrier with the KGF and EGFR inhibitor.

* * * * *